(12) United States Patent
Reynolds et al.

(10) Patent No.: US 7,553,287 B2
(45) Date of Patent: Jun. 30, 2009

(54) GUIDEWIRE HAVING AN EMBEDDED MATRIX POLYMER

(75) Inventors: Brian R. Reynolds, Ramsey, MN (US); James S. Sharrow, Bloomington, MN (US)

(73) Assignee: Boston Scientific Scimed, Inc., Maple Grove ( * ) Notice: Subject to any disclaimer, the term of this patent is extended or adjusted under 35 U.S.C. 154(b) by 619 days.

(21) Appl. No.: 10/699,051

(22) Filed: Oct. 30, 2003

(65) Prior Publication Data
US 2005/0096567 A1 May 5, 2005

(51) Int. Cl.
*A61M 25/00* (2006.01)
*A61B 6/00* (2006.01)
*A61B 1/00* (2006.01)
*A61B 1/04* (2006.01)
*B29D 28/00* (2006.01)
*D02G 1/20* (2006.01)
*D02J 1/22* (2006.01)
*B21C 1/00* (2006.01)
*B21C 23/08* (2006.01)
*B21F 1/00* (2006.01)
*B23P 11/02* (2006.01)
*B23P 25/00* (2006.01)
*B23P 11/00* (2006.01)

(52) U.S. Cl. .................... 600/585; 600/431; 600/432; 600/433; 600/434; 600/114; 600/121; 600/129; 600/108; 600/103; 264/103; 29/446; 29/447; 29/458; 29/517; 29/33 F; 29/34 D

(58) Field of Classification Search .................. 600/585, 600/431, 432, 433, 434, 114, 121, 129, 108; 264/103; 29/446, 447, 458, 517, 33 F, 34 D
See application file for complete search history.

(56) References Cited

U.S. PATENT DOCUMENTS

| | | | |
|---|---|---|---|
| 4,764,324 A | * | 8/1988 | Burnham ..................... 264/103 |
| 4,922,924 A | | 5/1990 | Gambale et al. |
| 4,934,380 A | | 6/1990 | de Toledo |
| 5,095,915 A | | 3/1992 | Engelson |
| 5,238,004 A | | 8/1993 | Sahatjian et al. |
| 5,244,619 A | | 9/1993 | Burnham |
| 5,251,640 A | | 10/1993 | Osborne |
| 5,333,620 A | | 8/1994 | Moutafis et al. |

(Continued)

FOREIGN PATENT DOCUMENTS

EP    0 720 838 A1    7/1996
WO    WO 2004/075726 A2    9/2004

OTHER PUBLICATIONS

U.S. Appl. No. 10/699,312, to Brian R. Reynolds et al., filed Oct. 30, 2003.

*Primary Examiner*—Max Hidenburg
*Assistant Examiner*—Jeffrey G Hoekstra
(74) *Attorney, Agent, or Firm*—Crompton, Seager & Tufte, LLC

(57) ABSTRACT

A guidewire having an embedded matrix polymer construction and methods of making and using the same. The guidewire may include a core wire or member having a proximal region and distal region, a jacket disposed over the distal region, and a coil disposed over the jacket. The coil may include a coating and may be embedded within the jacket.

28 Claims, 4 Drawing Sheets

U.S. PATENT DOCUMENTS

| | | |
|---|---|---|
| 5,406,960 A | 4/1995 | Corso, Jr. |
| 5,433,200 A | 7/1995 | Fleischhacker, Jr. |
| 5,437,288 A | 8/1995 | Schwartz et al. |
| 5,452,726 A | 9/1995 | Burmeister et al. |
| 5,497,785 A | 3/1996 | Viera |
| 5,551,443 A | 9/1996 | Sepetka et al. |
| 5,636,642 A | 6/1997 | Palermo |
| 5,666,969 A | 9/1997 | Urick et al. |
| 5,749,837 A | 5/1998 | Palermo |
| 5,769,796 A | 6/1998 | Palermo et al. |
| 5,772,609 A | 6/1998 | Nguyen et al. |
| 5,827,201 A | 10/1998 | Samson et al. |
| 5,830,155 A | 11/1998 | Frechette et al. |
| 5,836,893 A | 11/1998 | Urick |
| 5,840,046 A | 11/1998 | Deem |
| 5,876,356 A | 3/1999 | Viera et al. |
| 5,885,227 A | 3/1999 | Finlayson |
| 5,897,819 A | 4/1999 | Miyata et al. |
| 5,910,364 A | 6/1999 | Miyata et al. |
| 5,951,494 A | 9/1999 | Wang et al. |
| 5,984,877 A | 11/1999 | Fleischhacker, Jr. |
| 5,984,878 A | 11/1999 | Engelson |
| 6,017,335 A | 1/2000 | Burnham |
| 6,019,736 A | 2/2000 | Avellanet et al. |
| 6,042,876 A | 3/2000 | Deem |
| 6,056,702 A | 5/2000 | Lorenzo |
| 6,106,485 A | 8/2000 | McMahon |
| 6,139,510 A | 10/2000 | Palermo |
| 6,245,030 B1 | 6/2001 | DuBois et al. |
| 6,251,085 B1 | 6/2001 | Tezuka |
| 6,251,086 B1 | 6/2001 | Cornelius et al. |
| 6,254,550 B1 | 7/2001 | McNamara et al. |
| 6,296,616 B1 | 10/2001 | McMahon |
| 6,340,441 B1 | 1/2002 | Meyer et al. |
| 6,390,992 B1 | 5/2002 | Morris et al. |
| 6,402,706 B2 | 6/2002 | Richardson et al. |
| 6,409,682 B1 | 6/2002 | Burmeister et al. |
| 6,409,683 B1 | 6/2002 | Fonseca et al. |
| 6,436,056 B1 | 8/2002 | Wang et al. |
| 6,461,311 B2 | 10/2002 | DuBois et al. |
| 6,488,637 B1 | 12/2002 | Eder et al. |
| 6,494,847 B1 | 12/2002 | Richardson et al. |
| 6,494,894 B2 | 12/2002 | Mirarchi |
| 6,496,894 B1 | 12/2002 | Fanning |
| 6,544,197 B2 | 4/2003 | DeMello |
| 6,602,207 B1 | 8/2003 | Mam et al. |
| 6,918,882 B2 * | 7/2005 | Skujins et al. .............. 600/585 |
| 7,074,197 B2 * | 7/2006 | Reynolds et al. ........... 600/585 |
| 2004/0143239 A1 * | 7/2004 | Zhou et al. .................. 604/524 |
| 2004/0167438 A1 * | 8/2004 | Sharrow .................... 600/585 |
| 2004/0167441 A1 * | 8/2004 | Reynolds et al. ........... 600/585 |

* cited by examiner

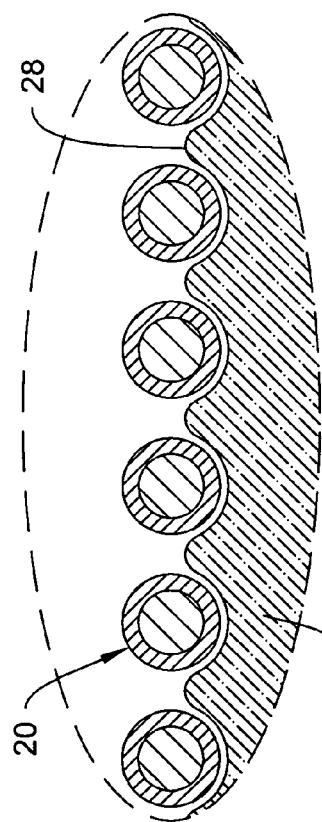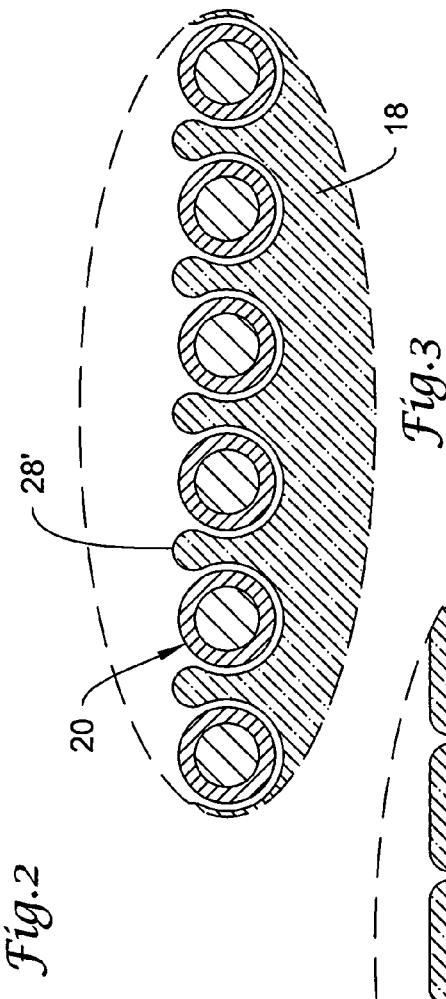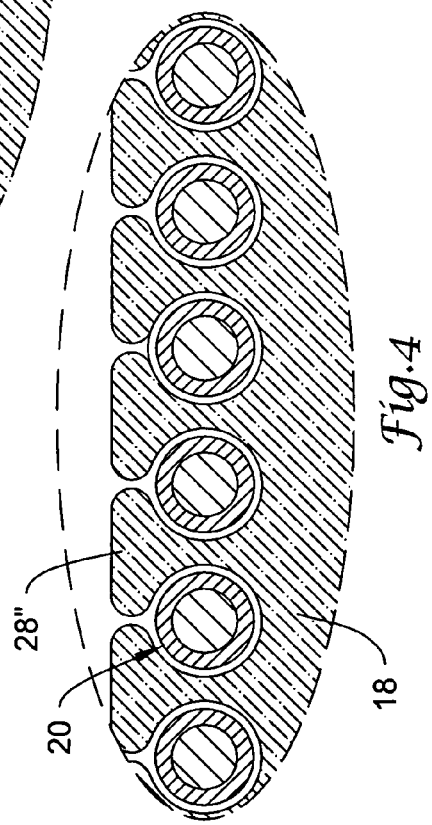

US 7,553,287 B2

GUIDEWIRE HAVING AN EMBEDDED MATRIX POLYMER

FIELD OF THE INVENTION

The present invention pertains to medical devices including guidewires. More particularly, the present invention pertains to guidewires with an embedded matrix polymer construction and refined traction characteristics.

BACKGROUND OF THE INVENTION

A wide variety of devices have been developed for medical use, for example, intravascular use. Some of these devices include guidewires, catheters, and other such devices that each have certain features and characteristics. Among the known medical devices, each has certain advantages and disadvantages. There is an ongoing need to provide alternative designs and methods for making and using medical devices with desirable characteristics and features.

SUMMARY OF THE INVENTION

The invention provides design, material, and manufacturing method alternatives for medical devices, for example, guidewires. In at least some embodiments, the guidewires include a core wire or member having a proximal region and distal region, a jacket disposed over the distal region, and a coil disposed over the jacket. The coil may include a coating and may be embedded within the jacket. These and some of the other features and characteristics of example embodiments are described in more detail below.

BRIEF DESCRIPTION OF THE DRAWINGS

FIG. 2 is an enlarged view of a portion of the guidewire illustrated in FIG. 1;

FIG. 3 is an alternative view of a portion of a guidewire;

FIG. 4 is another alternative view of a portion of a guidewire;

DETAILED DESCRIPTION OF THE PREFERRED EMBODIMENTS

Figure 1:
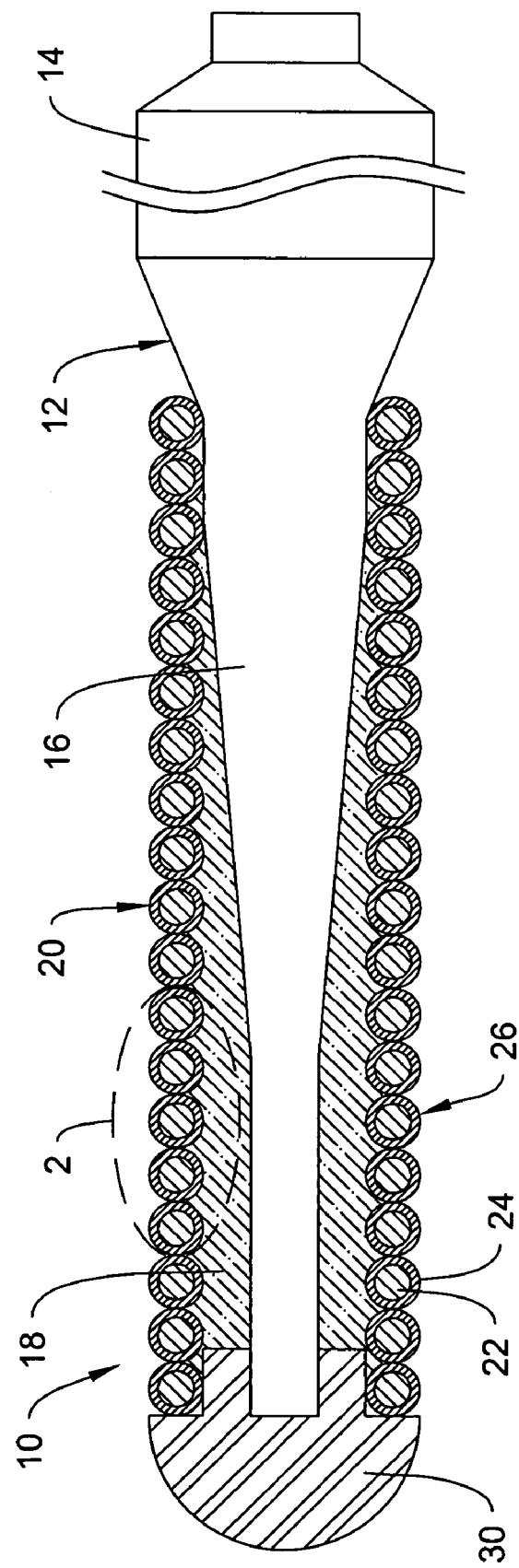
FIG. 1 is a partial cross-sectional side view of an example guidewire.

The following description should be read with reference to the drawings wherein like reference numerals indicate like elements throughout the several views. The detailed description and drawings illustrate example embodiments of the claimed invention.

FIG. 1 is a partial cross-sectional side view of an example medical device 10, depicted as a guidewire. Guidewire 10 may include a core wire or member 12 having a proximal region 14 and a distal region 16. A jacket 18 may be coupled to and/or disposed over core member 12, for example adjacent distal region 16. A coil 20 may be disposed over jacket 18. Although medical device 10 is depicted in FIG. 1 (and subsequent figures) as a guidewire, the invention is not intended to be limited to guidewires.

In some embodiments, coil 20 may be embedded within jacket 18. Being "embedded" within jacket 18 is understood to mean being disposed over jacket 18 in a manner that alters the shape of the outer surface of jacket 18. Thus, coil 20 is implanted or entrenched within jacket 18 and is not simply disposed on the top of jacket 18, completely submerged within jacket 18, or disposed between jacket 18 and another layer of material. Jacket 18 (in the absence of coil 20) may have or be manufactured to have a smooth outer surface. Embedding coil 20 into jacket 18 changes the shape of the outer surface as coil 20 is embedded therein. For example, embedding coil 20 into jacket 18 may result in jacket 18 wicking between the individual windings of coil 20. Accordingly, the shape of the outer surface of jacket 18 may be wave-like or otherwise include a series of peaks or alternating peaks and valleys. In some embodiments, this wave-like shape may generally conform to the shape of the inside surface of coil 20. The precise shape of the outer surface of jacket 18, however, may vary depending on a number of factors including the depth to which coil 20 is embedded. FIGS. 2-4 illustrate some examples of alternative shapes that may result.

The materials used for coil 20 and jacket 18 can vary greatly and may include any suitable material. It may be desirable, however, for the materials to be chosen based upon their ability to facilitate the embedding process and so as to achieve the desired level of embedding. For example, jacket 18 may be made from a thermoplastic material (i.e., a material whose viscosity changes with the induction of heat), a thermoplastic-like material, a thermoset material, combinations thereof, or the like. Some examples of these types of materials are listed below. Coil 20 can be made from fluorocarbon polymer or include a central core material 22 with a fluorocarbon coating 24. These materials may be desirable because of the ability of the thermoplastic material to "flow" or otherwise change shape when heated. Thus, coil 20 can be disposed adjacent the thermoplastic jacket 18 so that when heat is applied, the viscosity of jacket 18 changes and/or flows, which facilitates the embedding of coil 20 within jacket 18.

The embedding process (which may be described as thermal embedding or tension embedding) may vary, but generally includes disposing coil 20 over jacket 18 and heating. For example, coil 20 can be embedded within jacket 18 by winding the coil wire over jacket 18 while under tension. The coiling tension may allow coil 20 to recover in wound diameter (i.e., "shrink" to the diameter that coil 20 would have if the tension was relieved) when jacket 18 is heated. Therefore, the diameter of coil 20 reduces as heat is applied (i.e., the tension within coil 20 is relieved) and coil 20 moves inward into jacket 18 as the outer surface of jacket 18 wicks and/or otherwise changes shape to conform to the inside surface of coil 20 (or take on some other shape). Thus, the shifting of coil 20 and the alteration of jacket 18 results in the embedding of coil 20 within jacket 18.

When these materials are used, coil 20 is embedded within jacket 18 without melding together the two structures. Thus, a thermal bond is not defined that attaches coil 20 with jacket 18 along the region where coil 20 is embedded. This feature may be desirable because creating a direct bond between coil 20 and jacket 18 could create a position where the flexibility and/or bending characteristics of guidewire 10 are altered. This may create regions of inflexibility along guidewire 10, which may be undesirable. Instead of a direct thermal bond, coil 20 and jacket 18 may be secured in another manner. For example, coil 20 may be secured to jacket 18 by one or more mechanical connectors (e.g., disposed at opposing ends of coil 20), an adhesive, a thermal bond, a weld, or the like, or in any other suitable manner. In some embodiments, the wicking of jacket 18 between winding of coil 20 may secure the position of coil 20 relative to jacket 18. Securing coil 20 and jacket 18 via this wicking action may be desirable for a number of reasons. For example, securing coil 20 with the wicking action of jacket 18 may simplify the manufacturing process by eliminating the needs for additional manufacturing steps. In addition, the wicking action may also be desirable by providing compression and/or tension during the bending of guidewire 10 during an intervention. In other embodiments, securing coil 20 with jacket 18 may not be necessary.

The arrangement of jacket 18 and coil 20 may provide guidewire 10 with a number of desirable features. For example, embedding coil 20 within jacket 18 can help reduce the profile of guidewire 10. Thus, at least a portion of the extra outside diameter or profile that may have been added by disposing coil 20 onto jacket 18 can be eliminated. Accordingly, guidewire 10 can be easily sized for sensitive areas such as the central nervous system (where guidewire 10 may have an outside diameter of about 0.012 inches or less), for interventions near the heart (where guidewire 10 may have an outside diameter in the range of about 0.010 to about 0.020 inches or so), and for peripheral interventions (where guidewire 10 may have an outside diameter of about 0.014 inches to about 0.040 inches or more). Additionally, embedding coil 20 within jacket 18 can allow an outer surface 26 of coil 20 to define a ring-like or otherwise textured outer surface along a portion of the length of guidewire 10. This textured outer surface may improve traction between guidewire 10 and another device such as a catheter. For example, guidewire 10 may be used in conjunction with a number of different intravascular interventions where a catheter or other device is advanced over guidewire 10. At some point during the intervention, it may be desirable to maintain the position of guidewire 10 relative to the catheter. Because guidewires may be highly lubricous, maintaining their position within the catheter could pose a challenge. Accordingly, defining a textured surface on the outside of guidewire 10 may help improve the traction (e.g., by ratcheting on the catheter lumen or catheter tip) between guidewire 10 and the catheter lumen while adding or maintaining lubricity (e.g., by reducing the surface area touching the catheter lumen, thereby reducing friction). Additionally, the textured surface may also improve the traction between guidewire 10 and the tissue that it may interact with. For example, endothelial cells or other vessel tissue may grip or otherwise hold onto the textured surface and thereby improve traction.

Although it is stated above that jacket 18 may be made from a thermoplastic, any suitable polymer made be used. Some examples of suitable polymers (including thermoplastics) may include polytetrafluoroethylene (PTFE), ethylene tetrafluoroethylene (ETFE), fluorinated ethylene propylene (FEP), polyoxymethylene (POM), polybutylene terephthalate (PBT), polyether block ester, polyurethane, polypropylene (PP), polyvinylchloride (PVC), polyether-ester (for example, a polyether-ester elastomer such as ARNITEL® available from DSM Engineering Plastics), polyester (for example, a polyester elastomer such as HYTREL® available from DuPont), polyamide (for example, DURETHAN® available from Bayer or CRISTAMID® available from Elf Atochem), elastomeric polyamides, block polyamide/ethers, polyether block amide (PEBA, for example, available under the trade name PEBAX®), silicones, polyethylene (PE), Marlex high-density polyethylene, Marlex low-density polyethylene, linear low density polyethylene (for example, REXELL®), polyethylene terephthalate (PET), polyetheretherketone (PEEK), polyimide (PI), polyetherimide (PEI), polyphenylene sulfide (PPS), polyphenylene oxide (PPO), polysulfone, nylon, perfluoro(propyl vinyl ether) (PFA), low durometer thermal plastics (e.g., 25-50 Sure D), tungsten loaded thermal plastic compound, bismuth subcarbonate loaded thermal plastic compound, barium sulfate loaded thermal plastic compound, other suitable materials, or mixtures, combinations, copolymers thereof, polymer/metal composites, and the like. In some embodiments, jacket 18 can be blended with a liquid crystal polymer (LCP). For example, the mixture can contain up to about 5% LCP.

Coil 20 may be made from a solid fluorocarbon material such as PTFE or otherwise include outer coating 24 that is made from a fluorocarbon. A number of other materials may be used. For example, coil 20 may be made from a molecularly oriented high modulus and high melt index thermal plastic, a polymer clad tungsten or stainless steel wire (that is unlikely to thermally recover with heat), and the like, or any other suitable material including any of those listed herein. Coil 20 may also vary in size, length, shape, pitch, and the like. For example, coil 20 could have a generally round cross-sectional shape, a flattened ribbon-like shape, or any other suitable shape. Coil may extend along only a region of guidewire 10 (e.g., along distal region 16, a portion thereof, or any other region) or along essentially the entire length of guidewire 10. The pitch may be constant or vary, and can include tightly pitched regions, loosely pitched regions, and combinations thereof.

The pattern in which coil 20 is embedded within jacket 18 may also vary. For example, FIG. 1 depicts coil 20 as being embedded along essentially the entire length of jacket 18. This arrangement, however, is not intended to be limiting because other arrangements are contemplated. For example, coil 20 may be embedded along only a portion of jacket 18. Alternatively, coil 20 may include regions that are embedded intermixed with regions that are not embedded.

It can be appreciated that coil 20 may be embedded to essentially any depth within jacket 18. As the depth to which coil 20 is embedded changes, the effect on the shape of the outer surface of jacket 18 changes. FIGS. 2-4 illustrate embodiments where coil 20 is embedded at differing depths. For example, FIG. 2 shows coil 20 embedded to a relatively shallow depth so that a plurality of relatively shallow peaks 28 are defined within jacket 18. As coil 20 is embedded deeper, the size and shape of peaks 28 changes. For example, FIG. 3 shows coil 20 embedded to a greater depth so that peaks 28' extend to a position adjacent the outer surface of coil 20. FIG. 4 shows coil 20 embedded to an even greater extent so that peaks 28" extend beyond coil and have enlarged heads at the peaks. It can be appreciated that any of these depths, any other suitable depth, or any combination of depths may be utilized without departing from the spirit of the invention.

Core member 12 may be made from any suitable material including metals, metal alloys, polymers (including any of those listed herein), or any other suitable material. Some examples of suitable metals and metal alloys include stainless steel, such as 304V, 304L, and 316L stainless steel; alloys including nickel-titanium alloy such as linear elastic or superelastic (i.e., pseudoelastic) nitinol; nickel-chromium alloy; nickel-chromium-iron alloy; cobalt alloy; tungsten or tungsten alloys; MP35-N (having a composition of about 35% Ni, 35% Co, 20% Cr, 9.75% Mo, a maximum 1% Fe, a maximum 1% Ti, a maximum 0.25% C, a maximum 0.15% Mn, and a maximum 0.15% Si); hastelloy; monel 400; inconel 625; or the like; or other suitable materials.

In at least some embodiments, portions or all of core member 12, or other structures included within the guidewire 10 may also be doped with, made of, or otherwise include a radiopaque material. Radiopaque materials are understood to be materials capable of producing a sufficiently bright image on a fluoroscopy screen or another imaging technique during a medical procedure. This image aids the user of guidewire 10 in determining its location. Some examples of radiopaque materials can include, but are not limited to, gold, platinum, palladium, tantalum, tungsten alloy, polymer material loaded with a radiopaque filler, and the like. Additionally, core member 12 and/or guidewire 10 may include one or more marker bands or coils that include a radiopaque material.

In some embodiments, a degree of MRI compatibility can be imparted into guidewire 10. For example, to enhance compatibility with Magnetic Resonance Imaging (MRI) machines, it may be desirable to make core member 12, or other portions of guidewire 10, in a manner that would impart a degree of MRI compatibility. For example, core member 12, or portions thereof, may be made of a material that does not substantially distort the image and create substantial artifacts (artifacts are gaps in the image). Certain ferromagnetic materials, for example, may not be suitable because they may create artifacts in an MRI image. Core member 12, or portions thereof, may also be made from a material that the MRI machine can image. Some materials that exhibit these characteristics include, for example, tungsten, Elgiloy, MP35N, nitinol, and the like, and others.

Proximal region 14 and distal region 16 of core member 12 can be made of the same material, or in some embodiments, can include portions or sections made of different materials. In some embodiments, the material used to construct core member 12 is chosen to impart varying flexibility and stiffness characteristics to different portions of guidewire 10. For example, proximal region 14 and distal region 16 may be formed of different materials, for example materials having different moduli of elasticity, resulting in a difference in flexibility. In some embodiments, the material used to construct proximal region 14 can be relatively stiff for pushability and torqueability, and the material used to construct distal region 16 can be relatively flexible by comparison for better lateral trackability and steerability. For example, proximal region 14 can be formed of straightened 304v stainless steel wire or ribbon, and distal region 16 can be formed of a straightened super elastic or linear elastic alloy, for example a nickel-titanium alloy wire or ribbon.

The lengths of regions 14/16 (and/or the length of guidewire 10) are typically dictated by the length and flexibility characteristics desired in the final medical device. For example, proximal region 14 may have a length in the range of about 20 to about 300 centimeters or more and distal section 16 may have a length in the range of about 3 to about 50 centimeters or more. It can be appreciated that alterations in the length of regions 14/16 can be made without departing from the spirit of the invention.

Regions 14/16 can have a solid cross-section, but in some embodiments, can have a hollow cross-section. In yet other embodiments, regions 14/16 can include combinations of areas having solid cross-sections and hollow cross sections. Moreover, regions 14/16 can be made of rounded wire, flattened ribbon, or other such structures having various cross-sectional geometries. The cross-sectional geometries along the length of regions 14/16 can also be constant or can vary. For example, FIG. 1 depicts regions 14/16 as having a round cross-sectional shape. It can be appreciated that other cross-sectional shapes or combinations of shapes may be utilized without departing from the spirit of the invention. For example, the cross-sectional shape of regions 14/16 may be oval, rectangular, square, polygonal, and the like, or any suitable shape.

As shown in FIG. 1, distal region 16 may include one or more tapers or tapered regions. In some embodiments distal region 16 may be tapered and have an initial outside size or diameter that can be substantially the same as the outside diameter of proximal region 14, which then tapers to a reduced size or diameter. The tapered regions may be linearly tapered, tapered in a curvilinear fashion, uniformly tapered, non-uniformly tapered, or tapered in a step-wise fashion. The angle of any such tapers can vary, depending upon the desired flexibility characteristics. The length of the taper may be selected to obtain a more (longer length) or less (shorter length) gradual transition in stiffness. Although FIG. 1 depicts distal region 16 as being tapered, it can be appreciated that essentially any portion of core member 12 and/or guidewire 10 may be tapered and the taper can be in either the proximal or the distal direction. As shown in FIG. 1, the tapered region may include one or more portions where the outside diameter is narrowing, for example, the tapered portions, and portions where the outside diameter remains essentially constant, for example, constant diameter portions. The number, arrangement, size, and length of the narrowing and constant diameter portions can be varied to achieve the desired characteristics, such as flexibility and torque transmission characteristics. The narrowing and constant diameter portions as shown in FIG. 1 are not intended to be limiting, and alterations of this arrangement can be made without departing from the spirit of the invention.

The tapered and constant diameter portions of the tapered region may be formed by any one of a number of different techniques, for example, by centerless grinding methods, stamping methods, and the like. The centerless grinding technique may utilize an indexing system employing sensors (e.g., optical/reflective, magnetic) to avoid excessive grinding of the connection. In addition, the centerless grinding technique may utilize a CBN or diamond abrasive grinding wheel that is well shaped and dressed to avoid grabbing core wire during the grinding process. In some embodiments, core member 12 (e.g., distal region 16) can be centerless ground using a Royal Master HI-AC centerless grinder.

A distal tip member 30 may be disposed at the distal end of guidewire 10. In some embodiments, tip member 30 may be attached to core member 12. Coil 20 may be disposed over a portion of tip member 30. Distal tip member 30 may comprise any suitable structure. For example, distal tip member 30 may include a tube with an atraumatic tip (e.g., a solder ball) coupled thereto. It can be appreciated that the form and configuration of tip member 30 may vary as is commonly known in the art.

Figure 5:
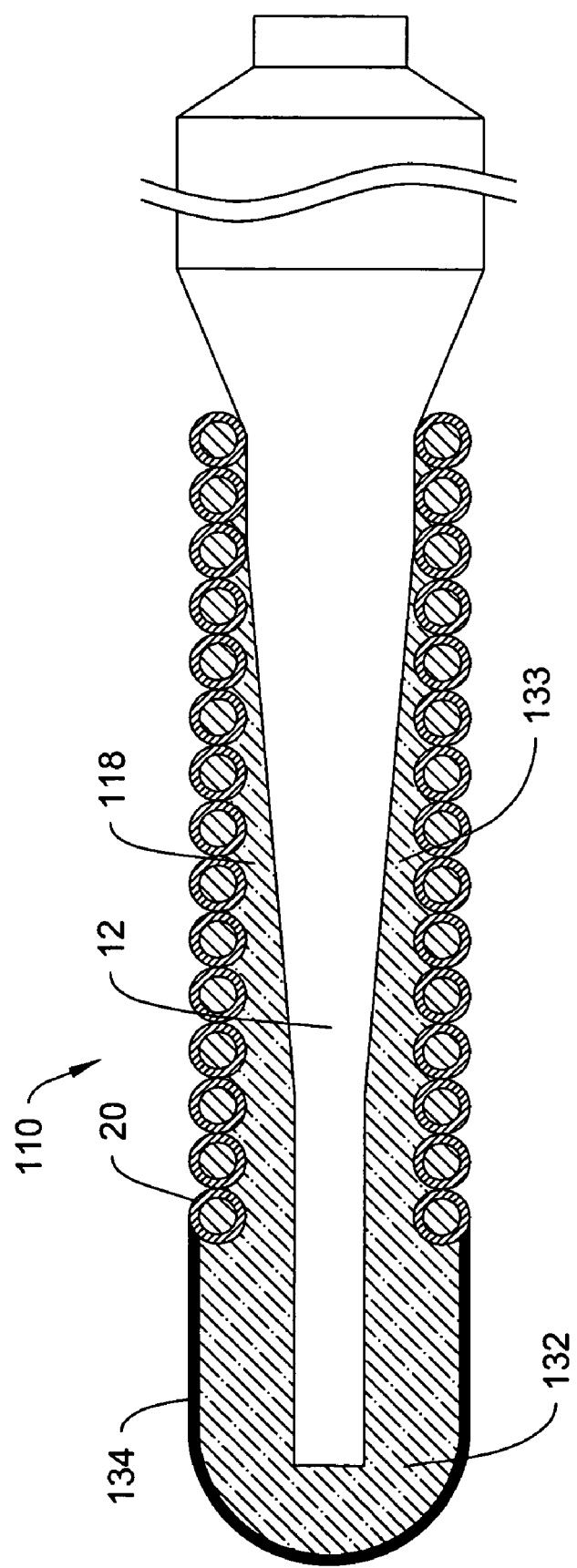
FIG. 5 is a partial cross-sectional side view of another example guidewire.

As suggested above, coil 20 may be disposed over essentially the entire length of jacket 18. However, this need not be the case as other arrangements are contemplated. For example, FIG. 5 illustrates another example guidewire 110, similar to others disclosed herein, where coil 20 extends along only a proximal section 133 of jacket 118. A distal section 132 of jacket 118, therefore, may define the distal tip of guidewire 110. According to this embodiment, the portion of distal section 132 that is disposed distally of coil 20 has a generally smooth surface and defines a smooth distal tip. This smooth distal tip may desirably impact the crossing ability of guidewire 110. In some embodiments, distal section 132 may include a coating 134, instead of coil 20. Coating 134 may comprise a lubricious, a hydrophilic, a protective, or other type of coating that may provide guidewire 110 with a number of desirable features. For example, hydrophobic coatings such as fluoropolymers provide a dry lubricity which improves guidewire handling and device exchanges. Lubricious coatings improve steerability and improve lesion crossing capability. Suitable lubricious polymers are well known in the art and may include silicone and the like, hydrophilic polymers such as polyarylene oxides, polyvinylpyrolidones, polyvinylalcohols, hydroxy alkyl cellulosics, algins, saccharides, caprolactones, and the like, and mixtures and combinations thereof. Hydrophilic polymers may be blended among themselves or with formulated amounts of water insoluble compounds (including some polymers) to yield coatings with suitable lubricity, bonding, and solubility. Some other examples of such coatings and materials and methods used to create such coatings can be found in U.S. Pat. Nos. 6,139,510 and 5,772,609, which are incorporated herein by reference.

Coating 134 may be formed, for example, by coating, by extrusion, co-extrusion, interrupted layer co-extrusion (ILC), or fusing several segments end-to-end over distal section 132. The layer may have a uniform stiffness or a gradual reduction in stiffness from the proximal end to the distal end thereof. The gradual reduction in stiffness may be continuous as by ILC or may be stepped as by fusing together separate extruded tubular segments. The outer layer may be impregnated with a radiopaque filler material to facilitate radiographic visualization. Those skilled in the art will recognize that these materials can vary widely without deviating from the scope of the present invention.

Figure 6:
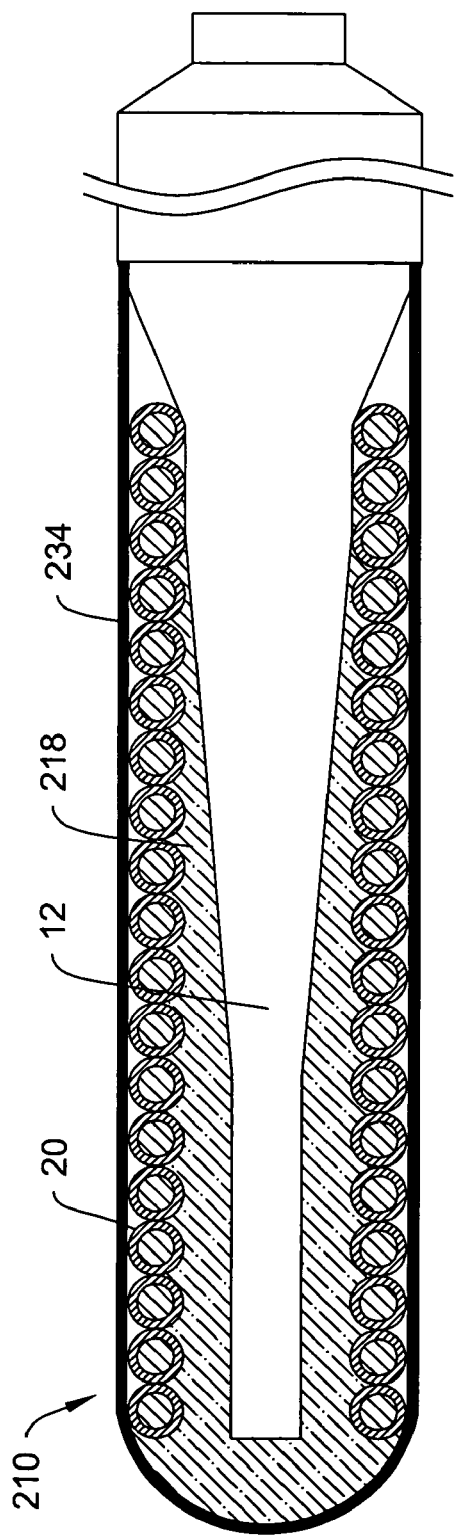
FIG. 6 is a partial cross-sectional side view of another example guidewire.

FIG. 6 illustrates another example guidewire 210, similar to guidewire 110, but with coating 234 extending proximally over coil 20. In some embodiments, coating 234 may follow the contour of coil 20 so that the ring-like texture defined by coil 20 can be maintained. Alternatively, coating 234 may follow only some or none of the contour of coil 20. According to these embodiments, the positioning, arrangement, and length of the textured regions defined by coil 20 can be varied.

Figure 7:
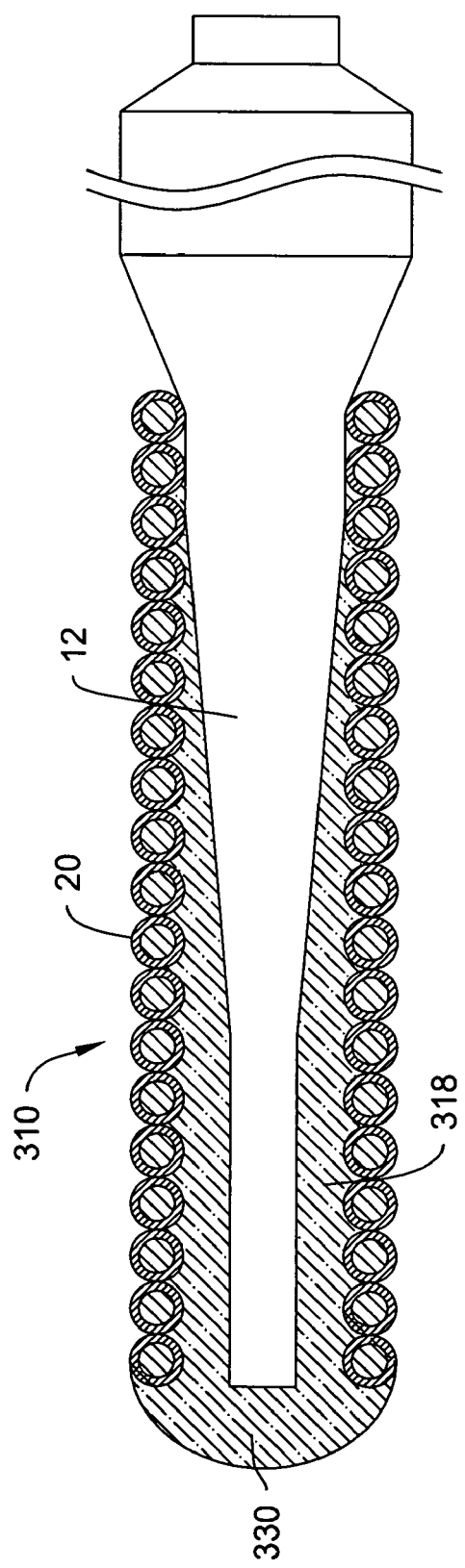
FIG. 7 is a partial cross-sectional side view of another example guidewire.

FIG. 7 depicts another example guidewire 310, similar to others disclosed herein, where jacket 318 extends distally beyond the distal end of core member 12 to define the distal tip 330 of guidewire 310. Coil 20 may be embedded within jacket 318 similarly to the other embodiments described above. Extending jacket 318 distally beyond the distal end of core member 12 may be desirable for a number of reasons. For example, this feature may simplify manufacturing of guidewire 310 by obviating the need to add another structure to define distal tip 330.

It should be understood that this disclosure is, in many respects, only illustrative. Changes may be made in details, particularly in matters of shape, size, and arrangement of steps without exceeding the scope of the invention. The invention's scope is, of course, defined in the language in which the appended claims are expressed.

What is claimed is:

1. A method for manufacturing a medical device, comprising the steps of:
   providing a core member having a proximal region, a distal region, and a tapered region between the proximal region and the distal region;
   disposing a polymer jacket over the distal region of the core member, the polymer jacket having a substantially smooth outer surface;
   winding a coil over the polymer jacket distal of the tapered region, wherein the coil is wound under tension over the polymer jacket; and
   heating the polymer jacket so that the coil moves inward into the polymer jacket, relieving tension within the coil and wicking a portion of the polymer jacket between adjacent windings of the coil, providing an outer surface of the polymer jacket relative to the coil in the medical device that has desirable flexibility characteristics;
   wherein the medical device, in a final manufactured form, includes an outermost surface having a helical ridge extending around a circumference of the outermost surface formed at least in part by a length of the coil wound over the polymer jacket distal of the tapered region.

2. The method of claim 1, wherein the polymer jacket includes a thermoplastic material and wherein the step of disposing the polymer jacket over the distal region of the core member includes disposing a thermoplastic polymer jacket over the distal region of the core member.

3. The method of claim 1, wherein the step of heating the jacket so that the coil moves inward into the polymer jacket, relieving tension within the coil and wicking a portion of the polymer jacket between adjacent windings of the coil includes embedding the coil within the jacket.

4. The method of claim 1, wherein the polymer jacket is not disposed over the proximal region of the core member.

5. A method for manufacturing a medical device, comprising the steps of:
   providing a core member having a proximal region, a distal region, and a tapered region between the proximal region and the distal region;
   disposing a polymer jacket over the distal region of the core member, the polymer jacket having a substantially smooth outer surface;
   winding a coil over the polymer jacket distal of the tapered region, wherein the coil is wound under tension over the polymer jacket;
   heating the polymer jacket so that tension within the coil is relieved and the outer surface of the polymer jacket wicks between adjacent windings of the coil, providing an outer surface of the polymer jacket relative to the coil in the final medical device that has desirable flexibility characteristics; and
   wherein the coil includes a fluorocarbon material and wherein the step of winding a coil over the polymer jacket includes winding the coil that includes a fluorocarbon material over the polymer jacket;
   wherein the medical device, in a final manufactured form, includes an outermost surface having a helical ridge extending around a circumference of the outermost surface formed at least in part by a length of the coil wound over the polymer jacket distal of the tapered region.

6. The method of claim 5, wherein the coil moves inward into the polymer jacket, thereby altering a shape of the outer surface of the polymer jacket.

7. A method for manufacturing a medical device, comprising the steps of:
   providing a core member having a proximal region and a distal region;
   disposing a polymer jacket over the distal region of the core member, the polymer jacket having a substantially smooth outer surface;
   winding a coil over the polymer jacket, wherein the coil is wound under tension over the polymer jacket;
   heating the polymer jacket so that tension within the coil is relieved and the outer surface of the polymer jacket wicks between adjacent windings of the coil, providing an outer surface of the polymer jacket relative to the coil in the medical device that has desirable flexibility characteristics; and
   wherein the coil includes a central metallic core material and an outer coating surrounding the central metallic core material, and wherein the step of winding a coil over the polymer jacket includes winding the coil that includes a central metallic core material and an outer coating surrounding the central metallic core material over the polymer jacket.

8. The method of claim 7, wherein the outer coating includes a fluorocarbon material.

9. The method of claim 7, wherein the coil moves inward into the polymer jacket, thereby altering a shape of the outer surface of the polymer jacket.

10. A method for manufacturing a guidewire, comprising the steps of:
   providing a core member having a proximal region, a distal region, and a tapered region between the proximal region and the distal region;
   disposing a jacket having an outer surface over the distal region of the core member;
   disposing a coil over the outer surface of the jacket distal of the tapered region; and
   embedding the coil into the outer surface of the jacket in a manner that alters a shape of the outer surface of the jacket so that the outer surface of the jacket wicks outward between adjacent windings of the coil, providing an outer surface of the jacket relative to the coil in the guidewire that has desirable flexibility characteristics;
   wherein the guidewire, in a final manufactured form, includes an outermost surface having a helical ridge extending around a circumference of the outermost surface formed at least in part by a length of the coil disposed over the outer surface of the jacket distal of the tapered region.

11. The method of claim 10, wherein the step of disposing a coil over the outer surface of the jacket includes disposing the coil over a proximal section of the jacket.

12. The method of claim 11, further comprising the step of disposing a covering over a distal section of the jacket.

13. The method of claim 10, further comprising the step of disposing a covering over the coil.

14. The method of claim 10, wherein the step of disposing the coil over the outer surface of the jacket includes winding the coil under tension about the outer surface of the jacket; and
   wherein during the step of embedding the coil into the outer surface of the jacket, the coil moves radially inward into the jacket, relieving tension within the coil and wicking a portion of the jacket outward between adjacent windings of the coil.

15. The method of claim 10, wherein the coil includes a central core material and an outer coating surrounding the central core material.

16. The method of claim 15, wherein the central core material is a metallic material.

17. The method of claim 10, wherein the polymer jacket is not disposed over the proximal region of the core member.

18. A method for manufacturing a guidewire, comprising the steps of:
   providing a core member having a proximal region, a distal region, and a tapered region between the proximal region and the distal region;
   disposing a jacket having an outer surface over the distal region of the core member;
   disposing a coil over the outer surface of the jacket distal of the tapered region;
   embedding the coil into the outer surface of the jacket in a manner that alters a shape of the outer surface of the jacket so that the outer surface of the jacket wicks outward between adjacent windings of the coil, providing an outer surface of the jacket relative to the coil in the guidewire that has desirable flexibility characteristics; and
   wherein the step of disposing a coil over the jacket includes winding the coil under tension about the outer surface of the jacket;
   wherein the guidewire, in a final manufactured form, includes an outermost surface having a helical ridge extending around a circumference of the outermost surface formed at least in part by a length of the coil disposed over the outer surface of the jacket distal of the tapered region.

19. The method of claim 18, wherein the coil includes a central core material and an outer coating surrounding the central core material.

20. The method of claim 19, wherein the central core material is a metallic material.

21. A method for manufacturing a guidewire, comprising the steps of:
   providing a core member having a proximal region, a distal region, and a tapered region between the proximal region and the distal region;
   disposing a jacket having an outer surface over the distal region of the core member;
   disposing a coil over the outer surface of the jacket distal of the tapered region;
   embedding the coil into the outer surface of the jacket in a manner that alters a shape of the outer surface of the jacket so that the outer surface of the jacket wicks outward between adjacent windings of the coil, providing an outer surface of the jacket relative to the coil in the guidewire that has desirable flexibility characteristics;
   wherein the step of disposing a coil over the jacket includes winding the coil under tension about the outer surface of the jacket; and
   wherein the step of embedding the coil within the jacket includes relieving the tension within the coil;
   wherein the guidewire, in a final manufactured form, includes an outermost surface having a helical ridge extending around a circumference of the outermost surface formed at least in part by a length of the coil disposed over the outer surface of the jacket distal of the tapered region.

22. The method of claim 21, wherein the coil includes a central core material and an outer coating surrounding the central core material.

23. The method of claim 22, wherein the central core material is a metallic material.

24. A method for manufacturing a guidewire, comprising the steps of:
   providing a core member having a proximal region, a distal region, and a tapered region between the proximal region and the distal region;
   disposing a thermoplastic jacket having an outer surface over the distal region of the core member;
   disposing a coil under tension about the outer surface of the jacket distal of the tapered region, the coil including a fluorocarbon material; and
   heating the thermoplastic jacket so that tension of the coil is relieved and the coil embeds within the jacket;
   wherein the guidewire, in a final manufactured form, includes an outermost surface having a helical ridge extending around a circumference of the outermost surface formed at least in part by a length of the coil disposed about the outer surface of the jacket distal of the tapered region.

25. The method of claim 24, wherein during the step of heating the thermoplastic jacket, the coil moves inward into the thermoplastic jacket, altering a shape of the outer surface of the thermoplastic jacket.

26. The method of claim 24, wherein the polymer jacket is not disposed over the proximal region of the core member.

27. A method for manufacturing a guidewire, comprising the steps of:
providing a core member having a proximal region, a distal region, and a tapered region between the proximal region and the distal region;
disposing a thermoplastic jacket having an outer surface over the distal region of the core member, the jacket having a proximal section and a distal section;
disposing a coil under tension about the proximal section of the jacket distal of the tapered region, the coil including a fluorocarbon material;
heating the thermoplastic jacket so that tension of the coil is relieved and the coil embeds within the jacket; and
disposing a coating over the distal section of the jacket;
wherein the guidewire, in a final manufactured form, includes an outermost surface having a helical ridge extending around a circumference of the outermost surface formed at least in part by a length of the coil disposed about the proximal section of the jacket distal of the tapered region.

28. The method of claim 27, wherein during the step of heating the thermoplastic jacket, the coil moves inward into the thermoplastic jacket, altering a shape of the outer surface of the thermoplastic jacket.

* * * * *

UNITED STATES PATENT AND TRADEMARK OFFICE
CERTIFICATE OF CORRECTION

PATENT NO. : 7,553,287 B2
APPLICATION NO. : 10/699051
DATED : June 30, 2009
INVENTOR(S) : Brian R. Reynolds et al.

It is certified that error appears in the above-identified patent and that said Letters Patent is hereby corrected as shown below:

Column 8
Line 34, delete "final".

Signed and Sealed this

Twenty-ninth Day of December, 2009

David J. Kappos
*Director of the United States Patent and Trademark Office*